United States Patent [19]

Pagel

[11] Patent Number: 4,994,397

[45] Date of Patent: Feb. 19, 1991

[54] ELECTROSTATIC METHOD AND APPARATUS FOR ANALYZING LIQUID SAMPLES

[76] Inventor: Hayes L. Pagel, 1466 Avocado Rd., Oceanside, Calif. 92054

[21] Appl. No.: 357,790

[22] Filed: May 30, 1989

[51] Int. Cl.$^5$ ............................................. G01N 27/00
[52] U.S. Cl. .................................. 436/149; 204/406; 204/407; 324/453
[58] Field of Search ................. 436/149; 204/406, 407; 324/453

[56] References Cited

U.S. PATENT DOCUMENTS

| | | | |
|---|---|---|---|
| 4,282,481 | 8/1981 | Dunn | 324/446 X |
| 4,506,226 | 3/1985 | Luce et al. | 204/406 X |
| 4,871,427 | 10/1989 | Kolesar, Jr. | 324/443 |

Primary Examiner—Robert J. Warden
Assistant Examiner—Amalia L. Santiago
Attorney, Agent, or Firm—Frank D. Gilliam

[57] ABSTRACT

A method and apparatus for defining the molecular chemical make up of a liquid sample, based on electrostatic charges of emission. Three spaced electrodes are brought into contact with the surface of a liquid to be tested. Two electrodes are wired in series through a usual cone speaker to the terminals of an audio amplifier. A third electrode is wired in series through a variable oscillator to the amplifier auxiliary input terminal. This overall regenerative feedback circuit will result in unique patterns of coded pulses at the amplifier speaker output corresponding to the composition of the liquid, which can be observed on an oscilloscope or recorded and compared with known compositions. This apparatus can be useful in defining molecular diseases when the electrodes are touched to the wetted skin of an animal, plant tissue or blood sample. The apparatus can also be adapted to a neological method of electronic gene mapping.

19 Claims, 2 Drawing Sheets

ELECTROSTATIC METHOD AND APPARATUS FOR ANALYZING LIQUID SAMPLES

BACKGROUND OF THE INVENTION

This invention relates in general to the identification of the chemical composition of a liquid solution and, more specifically, to a device and method for producing a pattern of electrical pulses indicative of the composition of a liquid sample.

Until recently, chemical analysis of unknown solutions was performed by so-called "classical" or "wet" methods such as titrimetric techniques. Over the last 40 years, a number of physicochemical methods of chemical analysis have been developed, using electrical, optical, density, surface tension and other such physical properties. Large and complex devices are now used to determine chemical and physical characteristics of solutions by methods based on spectroscopic, electrochemical, chromatographic, chemical and nuclear properties.

In spectroscopy, a sample is typically subjected to intense radiation in the form of gamma rays, x-rays, ultraviolet or infrared radiation, etc. A unique diffraction pattern or spectrogram unique to each chemical compound is produced. This apparatus is very large and expensive and requires a highly trained operator.

In chromatography and electrophoretic methods, a sample is caused to move along a column or cell, with the extent of movement varying in accordance with the composition of the sample. A great deal of skill is required to interpret the pattern of bands produced. The equipment is complex and must be carefully operated to prevent incorrect results through contamination and the like.

Another method of chemical analysis, spectrophotometric analysis, is based on the absorption or attenuation by matter of electromagnetic radiation of selected wavelength or frequency. The absorption of radiation at different wavelengths is carefully measured and plotted as a pattern of peaks and valleys. The patterns produced by different compounds are unique. Again, the apparatus is large, expensive and requires highly skilled operators.

Thus, there is a continuing need for effective, light weight, portable apparatus for analyzing the chemical composition of liquid samples.

It is, therefore, an object of this invention to provide an apparatus that is compact, portable and simple and easy to use for the detection and identification of the composition of liquids using the electrostatic characteristics thereof.

Another object of this invention is to provide a method and apparatus which permits unique and distinctive electrical characteristics of molecules of various compositions in a liquid sample to be directly observed and to be recorded.

A further object of this invention is to provide a method and apparatus useful in the investigation of the surface electrostatic characteristic charges spontaneously emitted from the skin of living beings and plant life.

Other objects and advantages of this invention will become apparent upon reading this disclosure.

SUMMARY OF THE INVENTION

A method and apparatus for determining the chemical composition of liquid samples in comparison to experimentally established standards. Three electrodes are positioned in an adjacent relationship adapted to being brought simultaneously into contact with the surface of a liquid sample. A first electrode is connected to the speaker output connection of a conventional audio amplifier through a conventional cone speaker, which causes pulsations of a signal from the speaker connection. A second electrode is connected directly to the amplifier speaker output. A third electrode is connected to the amplifier auxiliary input connection through a variable oscillator.

While the precise action of the molecules of the materials in the liquid solution is not fully understood, it appears that the molecules are electrostatically attracted and repulsed to the positive and negative poles of the immersed electrodes which are then subject to electrostatic charging and discharging. This results in the electrodes emitting minute electrostatic pulses of electrical energy that flow to the voltage amplifier. This electrostatic effect like crackling charges, becomes audible as a "message" system of coded "pops" in the well, generally similar to codes using varying signal emission lengths, such as the Morse Code. Such electrostatic emissions in a fluid are recognized as stochastic random motions, sometimes called Brownian motion in colloidal fluids. Through the feedback circuit provided, these pulses are amplified and are observable on a conventional oscilloscope and may be recorded using a conventional audio recorder or graphic recorder. I have found that different compounds produce unique and distinct pulse patterns which, once determined for known compounds, will permit solutions having unknown compositions to be analyzed.

In addition to the analysis of the chemical composition of liquids, this apparatus and method is also useful in investigations into other electrical characteristics of liquids. For example, the various types of coded charges emitted at the surface of enzymes and the like, in the electrostatic conduction of nerve impulses at synaptic junctions, or between cell surface contact communications. Also, by replacing the liquid contacting electrode assembly with a probe equipped with a removable electrode head having three adjacent needle-like electrodes, electrical characteristics of living beings may be investigated by inserting the needle electrodes a short distance into the skin of a subject.

BRIEF DESCRIPTION OF THE DRAWING

Details of the invention, and of certain preferred embodiments thereof, will be further understood upon reference to the drawing, wherein.

DETAILED DESCRIPTION OF PREFERRED EMBODIMENTS

Figure 1:
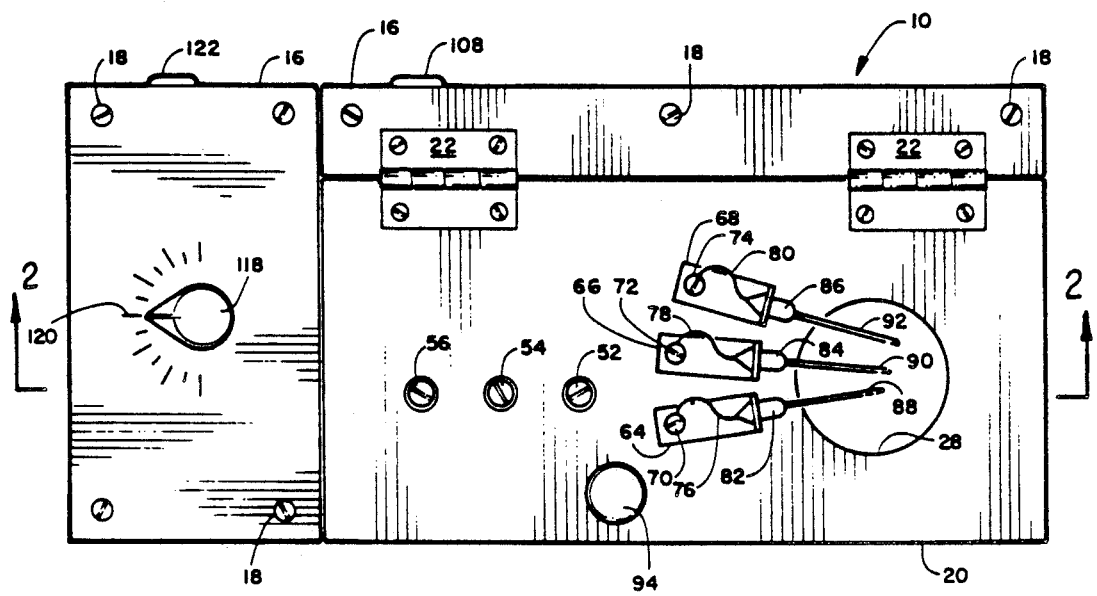
FIG. 1 is a schematic plan view of the apparatus of this invention.
Figure 2:
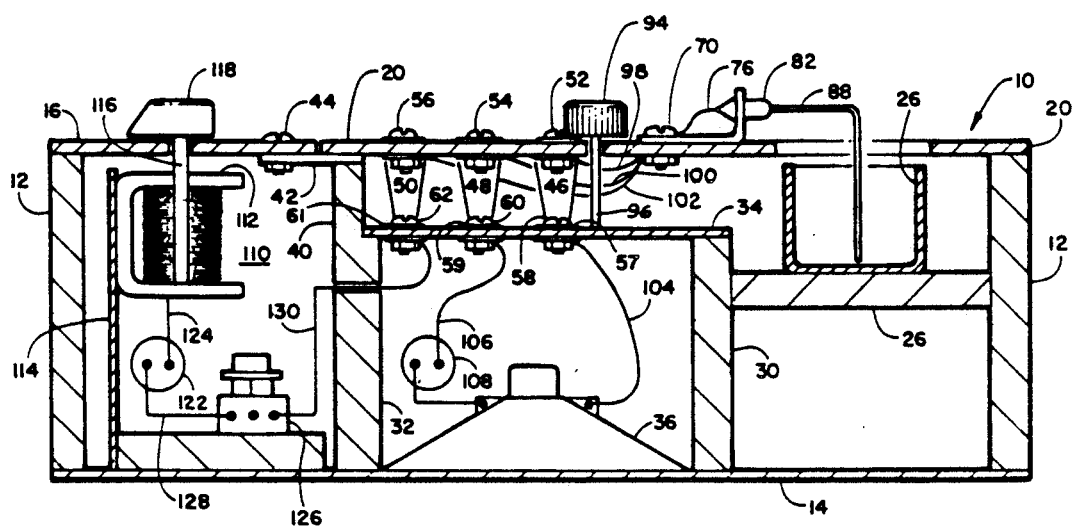
FIG. 2 is a vertical section view through the apparatus of FIG. 1, taken on line 2—2 in FIG. 1.

Referring now to FIGS. 1 and 2, considered together, there is seen a generally box-like housing 10, having sidewalls 12, a bottom closure 14 and a partial fixed cover 16. Cover 16 is held to sidewalls 12 by a plurality of screws 18 to permit convenient access to the interior of housing 10 when necessary.

A lid 20 covers the balance of the top of housing 10, hinged to cover 16 by a plurality of hinges 22.

Within housing 10 is located a support 24 to hold a liquid sample vessel 26 in alignment with an electrode well opening 28 in lid 20. An upstanding wall 30 holds one end of support 26 in position. Together with a second upstanding wall 32, wall 30 supports a plate 34.

A conventional audio speaker 36 is positioned between walls 30 and 32. Typically, speaker 36 may be a Model 20-231 from Calrad. Speaker 36 does not ordinarily emit any audible sounds. Rather, it acts as a highly refined electromagnetic choke. If desired, a small choke, about 4 ohms, or a reversed transformer input and output could be used in place of speaker 36. These, however, are not as effective as the dynamic action of speaker 36.

A small wall extension 40, fastened to a strip 42 (such as by glue) is secured to cover 16 by bolt 44. Wall extension 40 serves to support the edge of lid 20 in the fully closed position.

Figure 3:
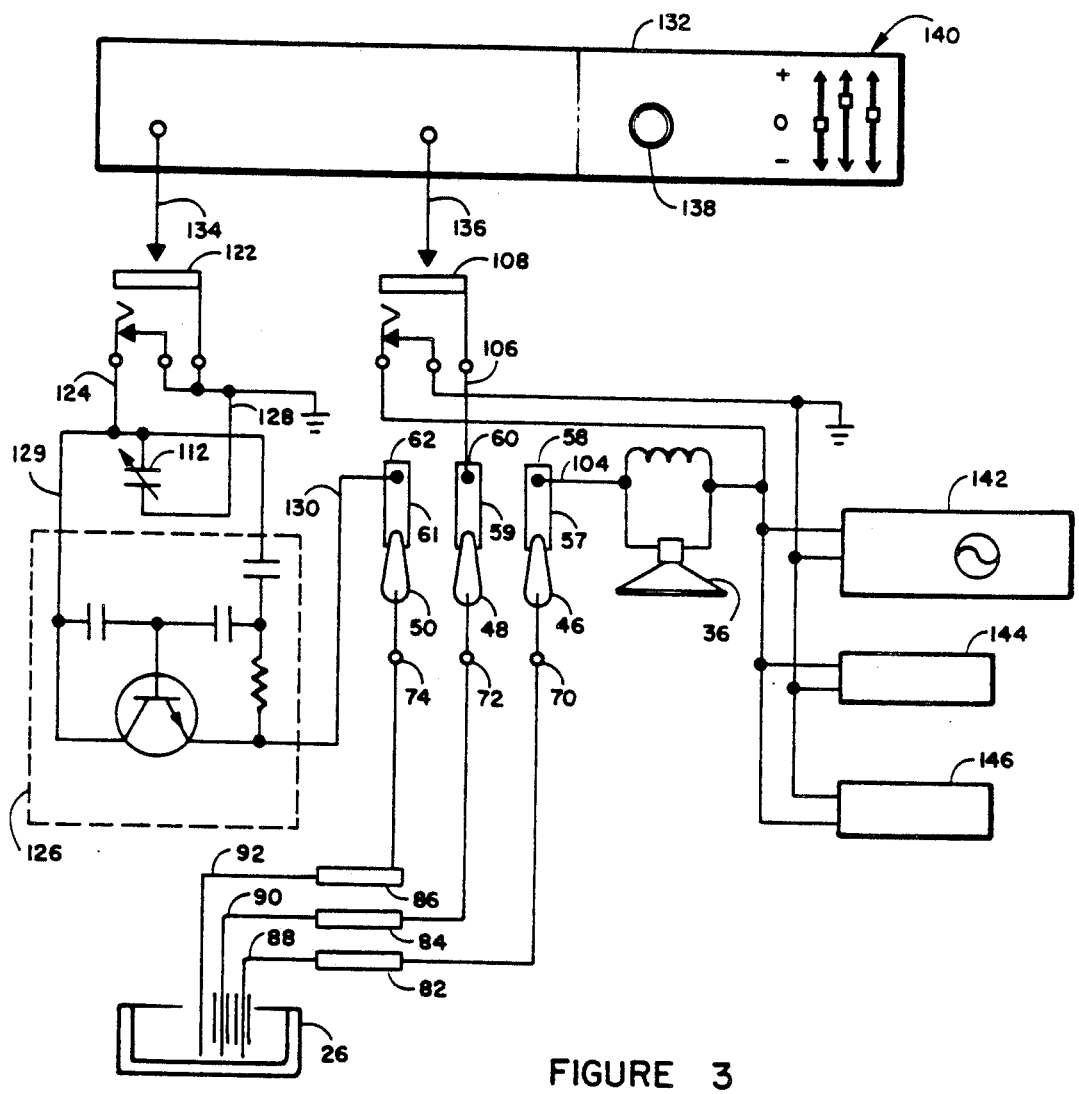
FIG. 3 is a schematic diagram of the electrical circuit of my apparatus.

Three thin metal electrical contacts 46, 48, and 50 (each having a leaf spring like configuration) are secured to lid 20 by bolts 52, 54 and 56, respectively. When lid 20 is closed (or nearly closed) the free ends of spring contacts 46, 48 and 50 contact metal strips 57, 59 and 61 (as best seen in FIG. 3) which are held to plate 34 by bolts 58, 60 and 62, respectively.

Three angular support members 64, 66 and 68 are secured to lid 20 by bolts 70, 72 and 74, respectively. Wires 76, 78 and 80 extend from bolts 70, 72 and 74, respectively, to corresponding electrode couplings 82, 84 and 86. The L-shaped electrodes 88, 90 and 92 are each a tight slip-fit into the corresponding couplings for ease of removal and replacement and are in electrical contact with the corresponding wires with the couplings. These electrodes are formed from any suitable conductor. The electrode materials should be resistant to corrosion by the liquid sample to be tested. In general, I have had good success where electrode 92 is aluminum and electrodes 88 and 90 are copper. The copper electrodes are preferably 12 gauge insulated copper wire with the ends sharpened to needle points for contacting the liquid in the well. Alongside, in contact with the insulation, is placed a bare 12 gauge aluminum wire for the auxiliary input. Preferably the electrodes are arranged in a parallel equally spaced arrangement with the distance between electrode tips being from about 2 to 12 millimeters.

When properly positioned, with the lid 20 nearly closed, the free ends of electrodes 88, 90 and 92 extend nearly to the bottom of sample vessel 26.

A threaded shaft 96 secured to knob 94 is threaded through lid 20 with the shaft end in contact with plate 34. Knob 94 can be rotated to slightly lift or lower lid 20, thereby adjusting the position of the ends of electrodes 88, 90 and 92 relative to the bottom of vessel 26.

Wires 98, 100 and 102 extend between corresponding pairs of bolts 52, 54 and 56 and electrode couplings 82, 84 and 86. Bolt 58 is connected by wire 104 to one connection of speaker 36. Bolt 54 is connected by wire 106 to one side of a jack 108, typically a conventional phone jack, with the second contact to jack 108 connected to the second side of speaker 36.

A compartment 110 is provided for the electronic components of my apparatus. A variable capacitor 112 is mounted on a support 114 with shaft 116 penetrating through cover 16. While any suitable variable capacitor may be used, I have found that excellent results are obtained using a 365 microfarad capacitor typically a Model 256 from Hammarlund. Capacitor 112 may be adjusted by rotating knob 118. A scale 120 may be provided for calibrating capacitor 112 positions.

One side of capacitor 112 is connected to one side of jack 122, typically a conventional phone jack, through wire 124. The second side of capacitor 112 is connected to ground through a second side of jack 122. The first side of jack 122 is also connected to electronic box 126 (the contents of are shown in FIG. 3 and which are described in detail below) through wire 129. Wire 130 connects electronic box 126 to bolt 62.

This test apparatus is light weight, sturdy and easily portable. It can be carried, with the other components of the test system described below, to any site for testing.

Details of the electronic components of this apparatus, and interconnections with other components, are provided in the schematic diagram of FIG. 3.

A conventional audio amplifier 132 is connected to my apparatus through jacks 108 and 112, as described above. Any suitable amplifier may be used. A typical amplifier is available from the Tandy Company under the Model MPA-40 designation. Typically, the output power of a suitable amplifier is preferably about 35 watts RMS, 200 Hz to 7 kHz. At the auxiliary input jack, the input impedance is preferable 50 ohms with an input sensitivity of about 150 mV. control frequency accuracy at 150 Hz, 1 kHz and 6 kHz should be within $+/-10\%$, with controls for varying attenuation at those frequencies over a $+/-12$ dB range.

Such an amplifier accepts a 150 mV auxiliary input through wire 134 from jack 112 and produces a speaker output signal (4 ohm output impedance) through wire 136 to jack 108. Speaker output volume is adjusted by volume control knob 138. Frequency balance can be adjusted by a set of frequency equalization controls 140. Typically, three such controls may be provided, one for the 150 Hz range, one for the 1 kHz range and one for the 6 kHz range.

Electronic box 126, as mentioned above, contains oscillator circuitry as shown. While any suitable oscillator may be used, the arrangement shown, using a 40233 transistor from RCA is preferred.

The output signal of the apparatus may be examined, evaluated and stored using any suitable device. For example, the output may be observed on a storage oscilloscope 142, be recorded on a conventional audio tape recorder 144 or be recorded on a conventional graphic strip recorder 146. A typical storage oscilloscope is the Model SS-5802 available from IWATSU. Graphic strip recorders include the WX-1100 from Graphtec.

Figure 4:
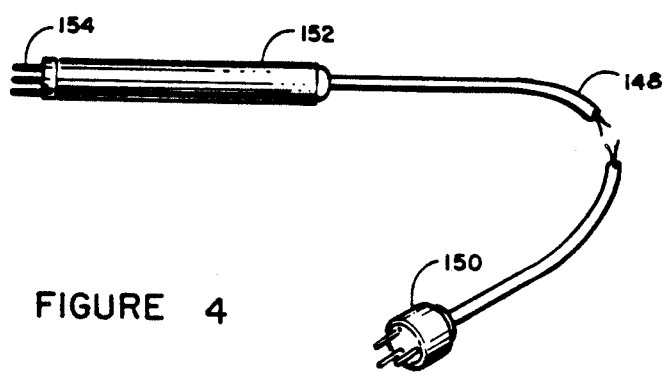
FIG. 4 is a perspective view of an alternative embodiment of the electrode arrangement useful with this apparatus.

An alternative embodiment to the electrode arrangement shown in FIG. 1 and 2 is illustrated in FIG. 4.

A flexible three conductor electrical cord 148 extends between a three connection plug 150 and a handpiece 152 having three needle-like pins 154 extending therefrom. Each needle is connected to one of the pins in plug 150. With this embodiment, bolts 52, 54 and 56 are connected to a jack (not shown) into which plug 150 may be inserted instead of the electrode assembly shown in FIGS. 1 and 2. Or, three separate, spaced pins could be used in place of plug 150, with each of those pins inserted in one of couplings 82, 84 and 86 in place of electrodes 88, 90 and 92. In either case, needles 154 function in the same way as electrodes 88, 90 and 92.

This flexible, extendible probe permits the operator to contact liquids which cannot be conveniently be placed in sample vessel 26, or to insert the needles slightly into the skin of a living subject to measure skin electrical characteristics.

Preferably, a water saturated gauze pad is laid over the skin for conductance as in osmosis or electrophoresis and the electrodes simply contact the wet gauze. Due to the speaker choke, there are no voltage sensations at the subject's skin.

Investigations of the nature of taste sensations on the tongue may be aided by measuring mouth saliva by contacting the tongue with the electrodes. For example, the tongue could be coated with a food and touched with the probe electrodes to obtain a taste reaction.

The operation of my apparatus in the performance of my method will be described in relationship to the illustrations of FIGS. 1-3.

Amplifier 132 is plugged into a 110 volt line with volume control 138 "off". Lid 20 is raised and vessel 26 is removed. Cable 134 is connected between the auxiliary input jack of amplifier 132 and jack 112 and cable 136 is connected between the speaker output jack of amplifier 132 and jack 108 of the test apparatus.

One or more of oscilloscope 142, tape recorder 144 and strip recorder 146 are connected in parallel to the amplifier output through conventional cables and jacks (not shown). For purposes of illustration, an oscilloscope 142 is considered to be connected. The scope 142 is switched "on".

Equalization balances 140 are set at the desired levels. Best levels can be established through tests of known liquids. In general, good results are obtained at a zero setting. Variable capacitor 112 is set at zero.

A small quantity of the liquid to be tested is placed in vessel 26. During calibration of the apparatus, a liquid of known composition is used, to establish "standard" patterns against which later patterns for unknown liquids can be compared. Generally, best results are obtained with very small samples, just enough to cover the bottom of vessel 26. The vessel is placed in the apparatus and lid 20 is lowered. The height of electrodes 88, 90 and 92 is adjusted by rotating knob 94 so that the electrodes just touch the surface of the liquid. With the minimum surface contact, the output signal will have lower frequency and higher amplitude. When the electrodes penetrate the liquid surface to a greater extent, the output signal frequency rises and the amplitude drops.

Volume control 138 is rotated to gradually increase gain. Care should be used to not increase gain too greatly, since eventually output signal distortion will occur.

While watching the oscilloscope, variable capacitor knob 118 is rotated to tune the band frequency for maximum pulsing of the beat frequencies in feedback resonance to the electrodes. This will vary according to the energy state and composition of the liquid. Variable capacitor 112 is adjusted for the best image on the scope for the measurement of the pulses, rhythms and the cycles as they pass in and out of phase.

The tape recorder 144 and/or strip recorder 146 may be turned on to record the waveforms. Waveforms may be recorded for a number of known materials. Waveforms for unknown liquids may be recorded and compared to known samples to determine the composition of the unknown samples. The apparatus may also be used for experimentation and investigation of electrical characteristics of various liquids and, using the alternative probe of FIG. 4, may be used for investigation of the electrical characteristics of the skin of living beings.

Other variations, applications and ramifications of this invention will occur to those skilled in the art upon reading the present disclosure. Those are intended to be included within the scope of this invention as defined in the appended claims.

I claim:

1. An apparatus for determining the composition of a liquid sample which comprises:
    an amplifier having a signal input connection means and speaker output connection means;
    means for directing signals from said speaker output connection means to an electromechanical speaker to cause pulsing of said speaker in response to variations in said speaker output signal;
    a first electrode having a tip adapted to contact a liquid sample;
    means directing the pulsed output signal from said speaker to said first electrode;
    a second electrode adjacent to said first electrode and having a tip adapted to contact said liquid sample;
    means connecting said second electrode to said speaker output connection means;
    a third electrode adjacent to said first and second electrodes, having a tip adapted to contact said liquid sample;
    means connecting said third electrode to the input of a variable oscillator means; and
    means connecting the output of said variable oscillator means to said amplifier input connection means;
    whereby the output of said amplifier speaker connection will have characteristics unique to a sample in contact with said electrodes.

2. The apparatus according to claim 1 further including manually adjustable variable capacitor means for varying the frequency of said variable oscillator means.

3. The apparatus according to claim 1 further including volume control means for manually varying the amplifier output to said speaker.

4. The apparatus according to claim 1 further including frequency equalization means for varying the amplifier output to said speaker at least three frequencies.

5. The apparatus according to claim 1 further including means for recording the amplifier output from said speaker.

6. The apparatus according to claim 5 wherein said recording means is an audio recorder.

7. The apparatus according to claim 5 wherein said recording means is a graphic strip recorder.

8. The apparatus according to claim 1 further including means for varying the depth said electrode tips extend into a liquid sample.

9. The apparatus according to claim 1 wherein said three electrode tips are spaced from about 2 to 12 millimeters from each other.

10. The apparatus according to claim 1 wherein said three electrodes are mounted in a parallel adjacent relationship at the end of a flexible probe and have sharp needle-like tips adapted to penetrate the skin of a living being.

11. A method for determining electrical characteristics of a liquid sample which comprises the steps of:
    providing a quantity of a liquid;
    bringing into contact with said liquid first, second and third spaced electrodes;

directing electrical signals from a speaker output connection of an audio amplifier through an electromagnetic speaker magnet to the first electrode;

directing signals from said speaker output connection directly to the second electrode;

directing output signals from said variable oscillator means to an auxiliary input connection of said amplifier; and observing characteristics of the signal from the amplifier speaker output connection;

whereby said signals from said amplifier speaker output connection have characteristics unique to the sample in contact with said electrodes.

12. The method according to claim 11 further including the step of adjusting the frequency of said variable oscillator by selectively adjusting a variable capacitor in the oscillator means.

13. The method according to clam 11 further including the step of selectively varying the volume of output signals from said speaker output connection.

14. The method according to claim 11 further including the step of selectively modifying said speaker output signal over at least three frequencies.

15. The method according to claim 11 wherein said signal from said amplifier speaker output connection is observed on a storage oscilloscope.

16. The method according to claim 11 including the further step of recording said signal from said amplifier speaker output connection.

17. The method according to claim 16 wherein said signal is recorded with an audio tape recorder.

18. The method according to claim 16 wherein said signal is recorded with a graphic strip recorder.

19. The method according to claim 11 including the step of adjusting the depth of penetration of said electrodes into said liquid.

* * * * *